United States Patent [19]

Tominaga et al.

[11] Patent Number: 4,957,370

[45] Date of Patent: Sep. 18, 1990

[54] METHOD AND APPARATUS FOR DETERMINING THE DEGREE OF OXIDATION OF AN OXIDE COATING

[75] Inventors: Mamoru Tominaga, Kawagoe; Leo Mori; Junetsu Akiyama, both of Yokohama, all of Japan

[73] Assignee: Kabushiki Kaisha Toshiba, Kanagawa, Japan

[21] Appl. No.: 404,050

[22] Filed: Sep. 6, 1989

Related U.S. Application Data

[63] Continuation of Ser. No. 282,863, Dec. 9, 1988, abandoned, which is a continuation of Ser. No. 112,060, Oct. 26, 1987, abandoned, which is a continuation of Ser. No. 748,305, Jun. 20, 1985, abandoned.

[30] Foreign Application Priority Data

Jun. 21, 1984 [JP] Japan ................................ 59-127843

[51] Int. Cl.⁵ .............................................. G01B 11/02
[52] U.S. Cl. ................................................... 356/381
[58] Field of Search ........................ 356/381, 382, 357

[56] References Cited

U.S. PATENT DOCUMENTS

| | | | |
|---|---|---|---|
| 3,017,512 | 1/1962 | Wolbert ........................ | 356/382 X |
| 3,737,237 | 6/1973 | Zurasky ........................ | 356/382 |
| 3,960,451 | 6/1976 | Wirz et al. .................... | 356/382 |
| 4,095,881 | 6/1978 | Maddox ........................ | 350/61 |
| 4,405,989 | 9/1983 | Tsukada et al. ................ | 356/381 |

FOREIGN PATENT DOCUMENTS

| | | | |
|---|---|---|---|
| 0011723 | 6/1980 | European Pat. Off. ............ | 356/357 |
| 2909400 | 9/1974 | Fed. Rep. of Germany ...... | 356/382 |
| 0101505 | 8/1981 | Japan ............................... | 356/381 |
| 166547 | 10/1982 | Japan . | |
| 0030605 | 2/1983 | Japan ............................... | 356/381 |
| 0001563 | 1/1985 | Japan ............................... | 356/382 |

OTHER PUBLICATIONS

"Three Color Cases Interferometer", Edwards, *IBM Technical Disclosure Bulletin*, vol. 16, #2, 7/1973.
L. Mori et al., "An Absolute Method of Color Temperature Measurement", Acta Chromatica, vol. 1, No. 3, pp. 93–102 (Oct., 1984).
ASTM T29-78 Standard Specification for Dumet Wire for Glass-to-Metal Seal Applications (May, 1978).

*Primary Examiner*—F. L. Evans
*Attorney, Agent, or Firm*—Finnegan, Henderson, Farabow, Garrett, and Dunner

[57] ABSTRACT

A method and apparatus determines the thickness of a copper oxide coating of an object by measuring the quantity of light reflected from the object in at least two wavelength zones, and then determining a value for a relationship between those quantities, for example, the ratio or difference of those quantities. The value is then compared to a predetermined, regular correspondence between such values and copper oxide thicknesses to determine the object's copper oxide thickness.

24 Claims, 8 Drawing Sheets

SPECTRAL TRANSMITTANCE CHARACTERISTICS
OF SHARP CUT-OFF FILTERS

SPECTRAL TRANSMITTANCE CURVES

METHOD AND APPARATUS FOR DETERMINING THE DEGREE OF OXIDATION OF AN OXIDE COATING

This application is a continuation of application Ser. No. 07/282,863, filed 12/09/88, now abandoned, which is a continuation of application Ser. No. 112,060 filed 10/26/87, now abandoned, which is a continuation of Ser. No. 748,305, filed on June 20, 1985, now abandoned.

BACKGROUND OF THE INVENTION

This invention relates generally to color analysis in manufacturing, and in particular, to the determination of the degree of oxidation of a copper oxide coating by color analysis.

Dumet wire is used in sealing lead-in wires for lamps or electronic devices. The thickness of the copper oxide coating of Dumet wire varies according to the degree of the oxidation, and the degree of oxidation is closely related to the sealability of Dumet wire to glass. To generate various grades of Dumet wire for different types of secondary processing, like welding or sealing with other materials, it is necessary during the manufacturing process to evaluate and then control the degree of oxidation of the Dumet wire based on the thickness of its oxide coating.

The thickness of the oxide coating is on the order of several microns and such fine thicknesses make it extremely difficult to test each product. It is therefore customary to classify the degree of oxidation on the basis of the color of the oxide coating since that color varies from reddish yellow to dark red depending upon the coating's thickness. The variation of color with oxidation is extremely subtle and the hue, saturation, and lightness of the color do not always vary regularly. Classification techniques which involve the visual comparison of the oxide color with a series of color samples require much time and labor and are not very accurate. Thus, more automatic techniques have been used to examine the color of the oxide.

Oxidation colors may be expressed numerically in such psychophysical quantities of color as tristimulus values X, Y, and Z, as well as by chromaticity coordinates x and y. The tristimulus values have been standardized by the Commission Internationale de l'Eclairage (CIE) and are defined as follows for a given sample having a spectral reflectance $\rho(\lambda)$ and which is illuminated by a light source having a spectral power distribution $S(\lambda)$:

$$\begin{bmatrix} X \\ Y \\ Z \end{bmatrix} = K \int_{380}^{760} S(\lambda)\rho(\lambda) \begin{bmatrix} \bar{x}(\lambda) \\ \bar{y}(\lambda) \\ \bar{z}(\lambda) \end{bmatrix} d\lambda;$$

where K is a normalizing factor equal to $$100 / \int_{380}^{760} S(\lambda)\bar{y}(\lambda)d\lambda.$$

In the equations for the tristimulus values shown above, Y is specifically referred to as luminous reflectance. Also, expressions $\bar{x}(\lambda)$, $\bar{y}(\lambda)$, and $\bar{z}(\lambda)$ are referred to as CIE color matching functions and the CIE has assigned the numerical values to varying wavelengths shown in FIG. 1.

The chromaticity coordinates x, y are defined as follows:

$$\begin{bmatrix} x \\ y \end{bmatrix} = \frac{1}{X + Y + Z} \begin{bmatrix} X \\ Y \end{bmatrix}.$$

By determining the spectral reflectance $\rho(\lambda)$ of a given sample with a spectrophotometer, the tristimulus values X, Y, and Z, the chromaticity coordinates x and y, and the luminous reflectance Y can be calculated on the basis of the known data of the spectral distribution $S(\lambda)$ of the light source used for illumination. This method of determination is known as spectrophotometric colorimetry.

Another method for determining the values mentioned above is called photoelectric tristimulus colorimetry and uses three photodetectors each of which includes color filters combined with a photocell. These filters possess spectral sensitivities matched to the values of the color matching functions $\bar{x}(\lambda)$, $\bar{y}(\lambda)$, and $\bar{z}(\lambda)$. In this method, the tristimulus values are determined directly from the outputs of the three photodetectors. Photoelectric tristimulus colorimetry, however, suffers from poor reproducibility in the photodetectors since the color filters used to match the sensitivities of the photodetectors to the color matching functions generally possess low transmitting levels. Also, it is extremely difficult to match color filters to the color matching functions exactly. Because of these disadvantages, most investigators who have needed highly accurate measurements have had to use the spectral photometric method described above despite its complexity, expense and difficulty.

In the spectrophotometric method, colorimetric values such as the chromaticity coordinates x and y and the luminous reflectance Y of the copper oxide coating should correspond to the degree of oxidation of copper. FIG. 2 shows the distribution of chromaticity, specifically coordinates x and y, values for nine copper oxide coating samples, a-i, each having a different degree of oxidation. Sample a has the smallest degree of oxidation and sample i has the greatest. As FIG. 2 demonstrates, although samples a-i show mutually approximating trends, they exhibit no conspicuous regular variation, except the slight indication that the chromaticity coordinate y decreases slightly with increasing oxidation degree. Thus, even using the colorimetric instrument in the spectral photometric method, it is extremely difficult to determine the degree of oxidation of a copper oxide coating accurately using chromaticity coordinates x and y.

Therefore, an object of this invention is apparatus and methods to determine the degree of oxidation of copper oxide coating easily and accurately.

Additional objects and advantages of this invention are set forth in part in the following description and in part are obvious from that description or may be learned by practice of the invention. The objects and advantages of the invention may be realized and obtained by the methods and apparatus in the appended claims.

SUMMARY OF THE INVENTION

The present invention overcomes the problems of the prior art and achieves the objects listed above by examining the ratios or differences of the quantities of reflected light in different wavelengths from an object with a copper oxide coating. The inventors have discovered that there is a regular variation between the degree of oxidation and certain relationships between the quantities of light in different wavelength zones.

Specifically, the apparatus of this invention for determining the thickness of the copper oxide coating of an object comprises: means for determining the quantities of light reflected from the object in different wavelength zones; and means, coupled to the determining means, for calculating a value representing a relationship between the quantities of reflected light and for thereby determining the thickness of the oxide coating of the object from a predetermined regular correspondence between oxide coating thicknesses and values for the relationship.

The system of this invention for testing manufactured items coated with copper oxide comprises: means for applying a copper oxide coating to the items; means for moving the items through said copper oxide coating means: means for illuminating the items with light; means for determining the quantities of light reflected from the items in different wavelength zones after the items have passed through the applying means; and means, coupled to the determining means, for calculating a value representing a relationship between the quantities of reflected light and for thereby determining the thickness of the copper oxide coating of the items from a predetermined regular relationship between copper oxide coating thicknesses and values for the relationship.

The method of this invention for determining the thickness of copper oxide coating of an object comprises the steps of measuring the quantity of reflected light from the object in different wavelength zones; calculating a value for a relationship between the quantities of reflected light; and comparing the value of the relationship to a predetermined regular correspondence between thickness values and relationship values to determine the thickness of said copper oxide coating.

The accompanying drawings, which are incorporated in and which constitute a part of this specification, illustrate an embodiment of the invention and together with that description explain the principles of the invention.

DESCRIPTION OF THE PREFERRED EMBODIMENT

Reference will now be made in detail to a presently preferred embodiment of this invention, an example of which is illustrated in the accompanying figures.

Figure 3:
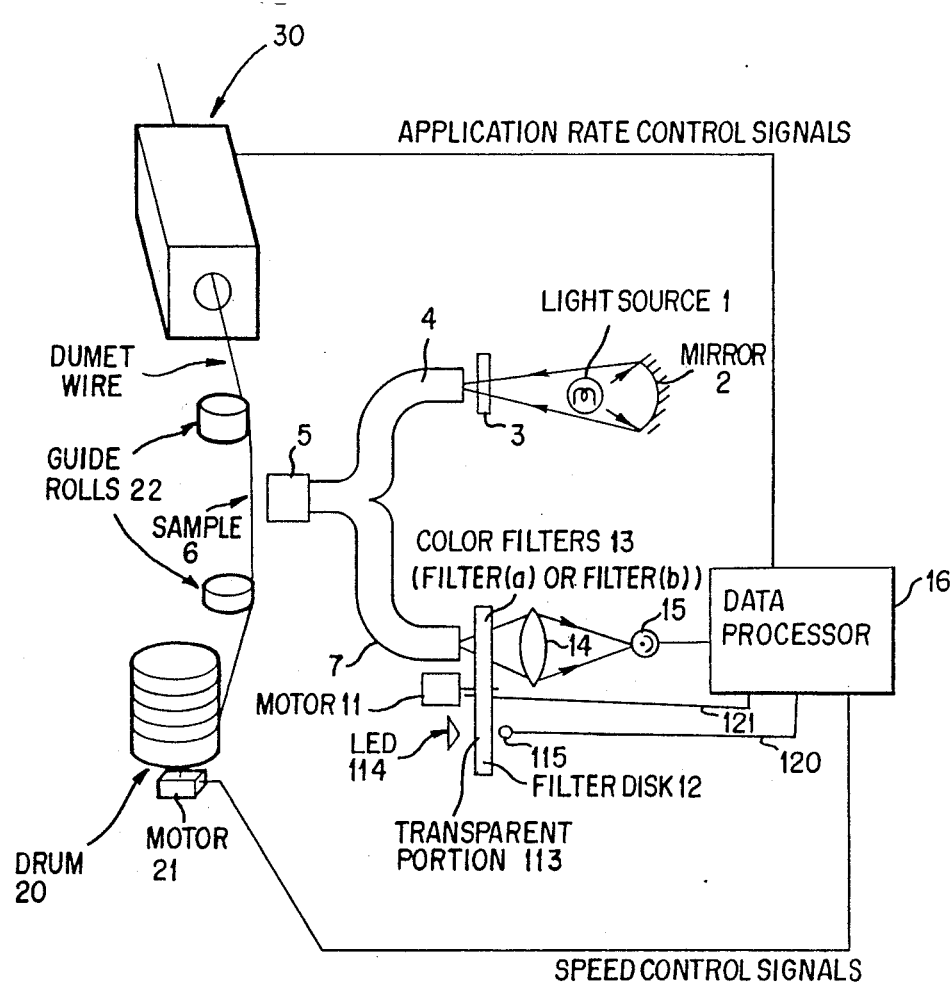
FIG. 3 is a schematic diagram of one embodiment of this invention.

FIG. 3 is a diagram of an apparatus according to this invention and will also be used in describing the method of this invention. Light source 1, one example of part of an illumination means according to this invention, is preferably an incandescent lamp having a prescribed spectral distribution $S(\Lambda)$. Reflective mirror 2, mounted behind light source 1, directs light from that source back toward illuminating light guide 4. Hot mirror (or cold filter) 3, mounted between source 1 and light guide 4, prevents heat, i.e. infrared radiation from light source 1 and mirror 2, from entering light guide 4. Illuminating light guide 4 directs the heatless light out of end part 5 of the light guide onto sample 6 which has a coating of copper oxide. The light reflected from sample 6 reenters end part 5 and passes through reflecting light guide 7 towards a photodetector.

Light guides 4 and 7 each comprise bundles of optical fibers which are randomly disposed at end part 5. The random arrangement ensures relatively uniform illumination of sample 6 and relatively uniform reception of the reflected light through guide 7.

Figure 4:
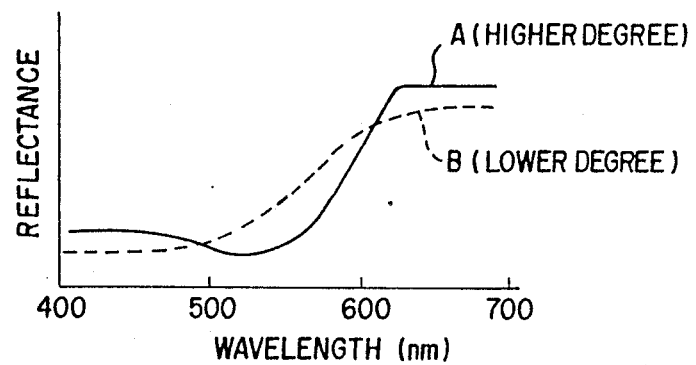
FIG. 4 is a diagram showing the spectral reflectance from Dumet wire samples with an oxide coating.

The light reflected from sample 6, after being illuminated as described above, possesses a certain spectral reflectance property which indicates the color of the sample. FIG. 4 shows the spectral reflectances for Dumet wire having two different thicknesses of copper oxide. The method and apparatus of this invention take advantage of the relationship between the quantities of reflected light at different wavelengths or in different wavelength zones.

In the preferred embodiment and method of this invention, the reflected light is divided into three wavelength zones: a short wavelength zone, a medium wavelength zone, and a long wavelength zone. The border between the short and medium wavelength zones is preferably in the neighborhood of 500 nm and the border between the medium and long wavelength zones is preferably in the neighborhood of 630 nm. The present invention uses the inventor's discovery that the spectral reflectance of a copper oxide coating in one of the predetermined zones increases or decreases depending upon the degree of oxidation of that coating. Specifically, a higher oxidation degree means an increase in the reflectance in the short and long wavelength zones and a decrease in the medium wavelength zone. As the degree of oxidation decreases, the spectral reflectance from that object has been found to decrease in the short and long wavelength zones and increase in the medium wavelength zone. Other materials may have similar properties and may similarly benefit from the present invention.

The present invention also takes advantage of the inventors' discovery that the degree of oxidation bears a determinable and regular correspondence with values for a specified relationship between (specifically the ratio or difference of) the quantities of reflected light in different wavelength zones. In particular, the ratios or differences should relate to the quantities in the medium or long wavelength zones or in the medium and short wavelength zones.

Figure 1:
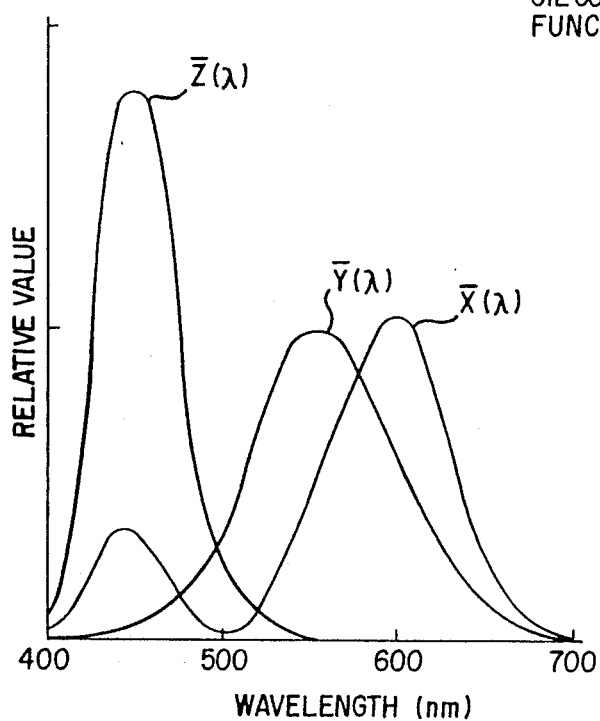
FIG. 1 is a diagram showing CIE color matching functions.
Figure 2:
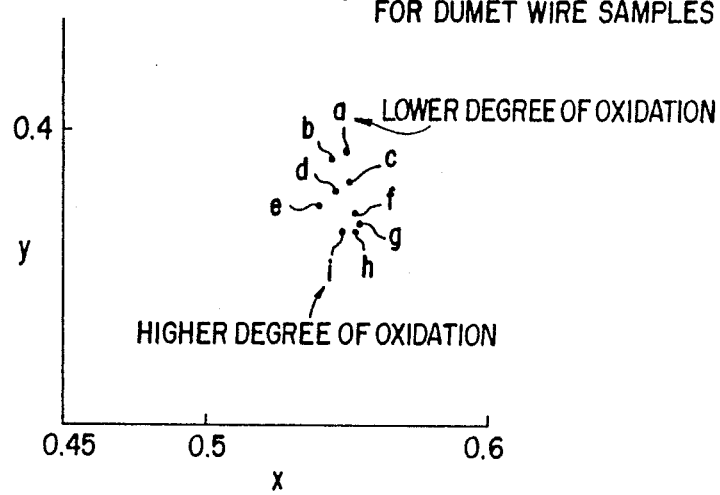
FIG. 2 is a diagram showing varying chromaticity values from samples having different degrees of oxidation.
Figure 5:
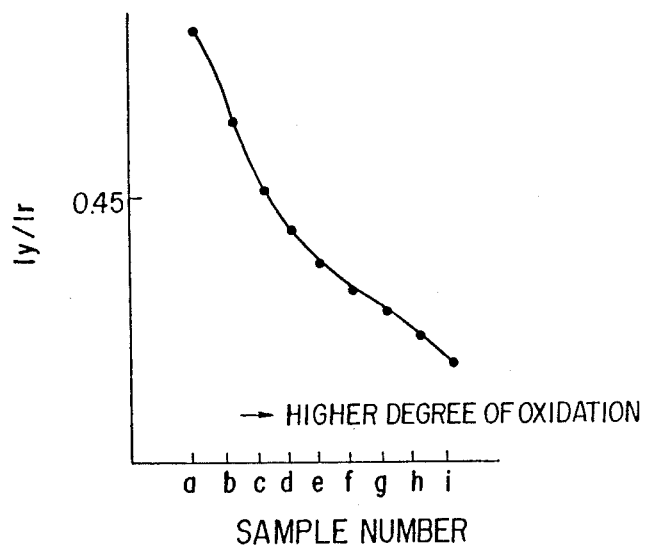
FIG. 5 is a diagram showing a relationship between the ratio of reflected light in two wavelength zones and the degree of oxidation of Dumet wire samples.

A regular correspondence, as used in the description of this invention, means that for each value of the defined ratio or difference, there is only one value for oxidation degree. Such a correspondence for Dumet wire is shown in FIG. 5, which reflects the results from tests conducted on Dumet wire samples denoted a-i having increasing degrees of oxidation. The samples a-i in FIG. 5, and their degrees of oxidation, correspond to the samples a-i in FIG. 2 and those degrees of oxidation.

In FIG. 5, $i_y$ refers to the quantity of reflected light received in the medium or yellow zone and $i_r$ refers to the quantity of light received in the long or red zone. The ratio $i_y/i_r$ in FIG. 5 is the ratio of the quantity of reflected light in the medium zone and the quantity of reflected light in the red zone. The regular relationship shown in FIG. 5 means that each value of $i_y/i_r$ corresponds to a unique value for oxidation degree. A similar regular relationship results from using the ratio $i_y/i_k$ or $i_y/(i_r+i_k)$. The value of $i_k$ reflects the quantity of light received in the short or blue zone. As will be explained in more detail, the present invention offers many advantages over the spectrophotometric colorimetry method which yields the non-regular relationship in FIG. 2.

In the preferred embodiment of this invention shown in FIG. 3, reflecting light guide 7 directs the light reflected by sample 6 into a first area. The present invention includes means for determining the quantities of light reflected by the sample into different wavelength zones. More particularly, in accordance with the present invention there is means in the first area for filtering light reflections into two wavelength zones. In the preferred embodiment of this invention, rotary filter disk 12 contains color filters 13, comprising filters 13a and 13b, and a transparent portion 113. Motor 11, which is rotatably mounted to disk 12, causes the filters 13 to pass through the path of the reflected light from guide 7 at a known cycle rate. After passing through filters 13, lens 14 focuses the light onto photodetector 15 which measures the intensities or quantities of the reflected light.

Figure 3A:
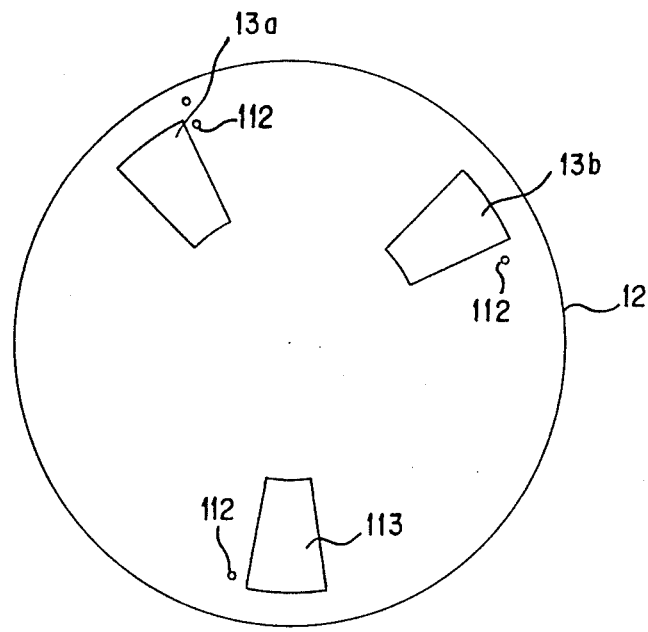
FIG. 3A is a diagram showing an embodiment of the color filters and disk in FIG. 3.
Figure 6:
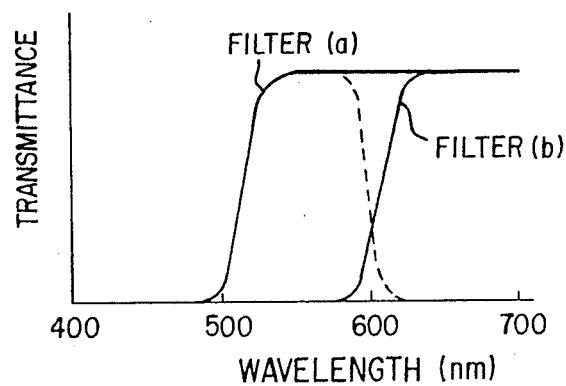
FIG. 6 is a diagram showing the spectral transmittance characteristics of sharp cut-off filters used in the embodiment shown in FIG. 3.

Color filters 13 preferably include at least two sharp-cut filters. A first sharp cut-off filter 13a has a transmission threshold in the neighborhood of 500 nm and a second sharp-cut filter 13b has a transmission threshold in the neighborhood of 630 nm. FIG. 6 shows the spectral transmittance characteristics of filters 13a and 13b. The placement of filters 13a and 13b on disk 12 is shown in greater detail in FIG. 3A. Disk 12 also has transparent portion 113 which serves two purposes. One purpose is to allow measurement of the full quantity of reflected light. Another purpose, which is described in greater detail below, is to facilitate synchronization of the filters' rotation with the rest of the apparatus in FIG. 3. Holes 112 in disk 12 may also be used for synchronization.

Photodetector 15 measures the intensity of the reflected light after it passes through either color filters 13 or transparent portion 113. The measured intensities of the reflected light after passing through filters 13a, 13b and transparent portion 113 and being converted into digital data are denoted $i_a$, $i_b$ and $i_O$. Data processing unit 16 reads the output of photodetector 15 and senses $i_a$, $i_b$, and $i_O$ by being in synchronism with the rotation of disk 12, and therefore with the insertion of filters 13a and 13b and transparent portion 113 into the path of the reflected light.

Such synchronism can be achieved in several ways. In FIG. 3, if motor 11 runs freely, data processor 16 remains in synchronism by sensing the cyclical rate of disk 12 using LED 114 and photodetector 115 which are aligned on opposite sides of disk 12. When transparent portion 113, or holes 112, move between LED 114 and photodetector 115, photodetector 115's output registers a pulse indicating the sensing of light from LED 114. Data processor 116, which is coupled to photodetector via line 120, then uses the pulse output of photodetector 115 to maintain synchronism.

Alternatively, motor 11 could be a step motor coupled to data processor 16 via line 121. Processor 16 in this configuration would send signals over line 121 to advance motor 11 by steps at the desired rate.

The present invention also includes means for calculating a value for the relationship between the quantities or intensities of the reflected light in the different wavelength zones. In the preferred embodiment, data processing unit 16 includes such means and determines the components of the reflected light in the short, medium and long wavelength zones, $i_k$, $i_y$ and $i_r$, respectively, from the values of $i_a$, $i_b$, and $i_O$. Since in the preferred embodiment, $i_b$ corresponds to the reflected light having wavelengths exceeding 630 nm, it is treated as the $i_r$ component for the long wavelength zone. Data processor 16 calculates the value $i_a-i_b$ as the $i_y$ component for the medium wavelength zone and the value $i_O-i_a$ is the $i_k$ component for the short wavelength zone. Of course, if different equipment is used, $i_y$, $i_r$, and $i_k$ can be determined directly.

Data processing unit 16 preferably either calculates one of the ratios $i_y/(i_r+i_k)$, $i_y/i_k$, or $i_y/i_r$, or one of the differences $i_y-(i_r+i_k)$, $i_y-i_k$, or $i_y-i_r$. The inventors have discovered that for copper oxide coating of Dumet wire each of these values has a regular correspondence with the degree of oxidation.

FIG. 5 shows the regular correspondence of the ratio $i_y/i_r$ with oxidation degree as determined by the samples a-i. The ratio of the reflected light in the two wavelength zones decreases as the degree of oxidation of the sample increases and vice versa. This correspondence is preferably predetermined either from known data or by use of this invention with calibrated samples.

The preferred apparatus and method of this invention derive the degree of oxidation of a Dumet wire sample by finding the ratio or difference of the reflected light value in different wavelength zones and applying that ratio or difference to a predetermined, regular relationship between those values and the degree of oxidation. Practice of the present invention, therefore, allows the degree of oxidation to be determined very accurately, quickly and efficiently. The apparatus and methods of this invention can thus contribute to effective quality control of production of items having copper oxide or other coatings.

In accordance with the present invention, process control is effected with means for applying a copper oxide coating to manufactured items, including sample 6, and means for moving the items through the copper oxide applying means. In the preferred embodiment, the copper oxide applying means includes apparatus 30, which is a conventional apparatus for applying a copper oxide coating to Dumet wire 31. Apparatus 30 can either have a fixed process rate or it can vary the rate that the copper oxide is applied in response to application rate control signals from data processor 16.

As shown in FIG. 3, a preferred embodiment of the moving means includes drum 20 and speed-controlled motor 21. Motor 21 controls the speed that drum 20 pulls the Dumet wire through apparatus 30 and around guide rolls 22. Data processing unit 16 controls the speed of motor 21, and thus the speed of drum 20, using speed control signals.

By controlling the speed of motor 21, and thus drum 20, the amount of oxidation on the Dumet wire can be increased or decreased. Slowing down drum 20 keeps the wire in the oxidation process of apparatus 30 longer, thereby causing increased oxidation. Conversely, speeding up drum 20 decreases oxidation of the wire since the Dument wire is exposed to the oxidation process in apparatus 30 for a shorter period of time.

Alternatively, processor 16 may also control the degree of oxidation of the Dumet wire by sending application rate control signals. Apparatus 30 would then set its process rate in accordance with these signals to obtain the desired degree oxidation for the Dumet wire.

The advantage of the present invention is that it allows the degree of oxidation of the Dumet wire to be controlled automatically and very accurately. An operator or production manager would merely enter the desired degree of oxidation into data processor 16. Once the production is started, portions of the Dumet wire would be sequentially analyzed and their degree of oxidation would be determined as indicated above. If the degree of oxidation of the Dumet wire samples exceeded the desired value, then the data processing unit 16 would direct motor 21 to accelerate drum 20 or processor 16 would direct apparatus 30 to reduce the process rate. If the degree of oxidation of the Dumet wire was below the desired value 16, processor 16 would then slow down motor 21 and drum 20 to increase the degree of oxidation or processor 16 would cause apparatus 30 to increase its process rate.

Figure 7:
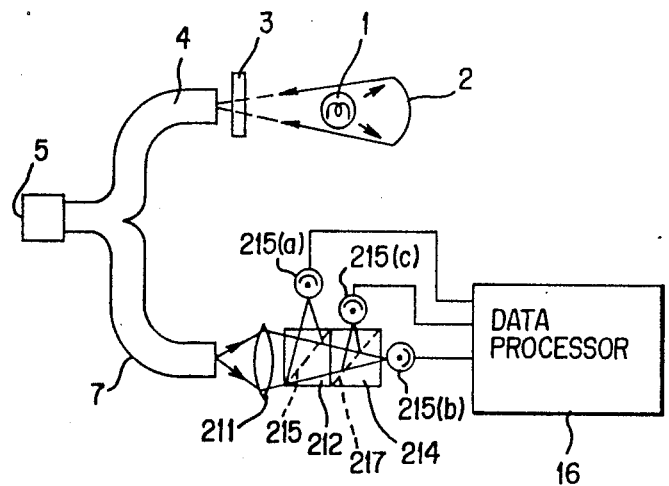
FIG. 7 is a schematic diagram of another embodiment of this invention.

Another embodiment of the present invention which does not require rotating color filters is shown in FIG. 7. Elements which are the same as those shown in FIG. 3 are designated by the same numbers and will not be described again. Reflected light travels via light guide 7 toward the light detectors. After passing through lens or light condensor 211, the focused light strikes the light receiving surfaces of photodetectors 215(a), 215(b), and 215(c) by means of reflecting surface 213 of prism-type beam splitter 212 and reflecting surface 217 of prism-type beam splitter 214.

Reflecting surface 213 is a blue-reflecting dichroic mirror which reflects light having wavelengths shorter than 500nm. Photodetector 215(a) detects the component of the reflected light in the short wavelength zone. Reflecting surface 217 of beam splitter 214 is a red-reflecting dichroic mirror which reflects light having wavelengths longer than 630nm. Photodetector 215(b) detects the light which passes through the reflecting surface 217, such light being the component of the reflected light in the medium wavelength zone. Photodetector 215(c) detects the light which is reflected from surface 217, or, in other words, the component of the reflected light in the long wavelength region.

The components of the reflected light measured by photodetectors 215(a), 215(b), and 215(c) correspond respectively to $i_a$, $i_b$, and $i_c$, and are inputs to data processor 16. Data processor 16 computes the ratios or differences and takes the actions as have been indicated in the description accompanying the apparatus in FIG. 3.

Beam splitters are commonly used to divide an incident light beam into two emerging beams. The principles of beam splitters are described in detail by G. Wyszecki and W. Stiles on pages 41–49 of a book entitled COLOR SCIENCE (1982), which is herein incorporated by reference.

Figure 7A:
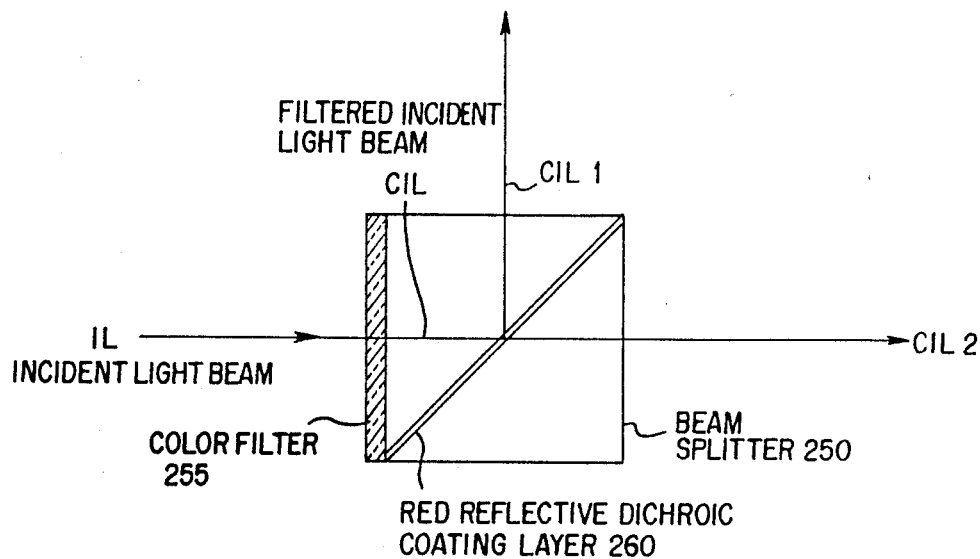
FIG. 7A shows one beam splitter to explain its operation.
Figure 7B:
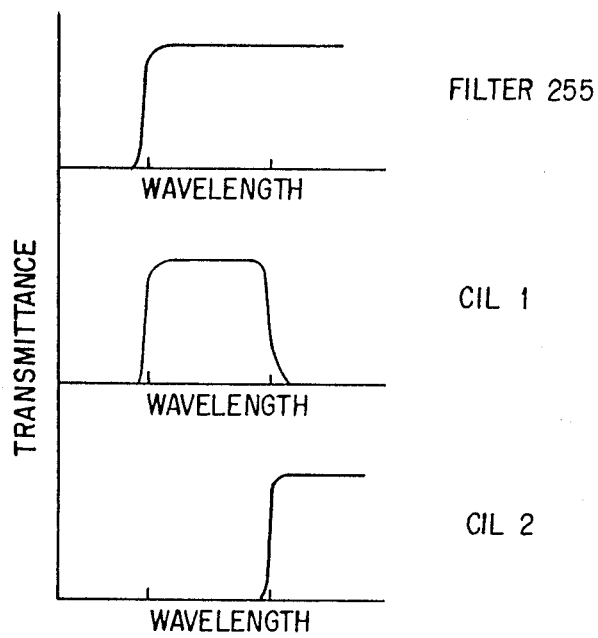
FIG. 7B shows spectral of transmittance curves for the beam splitter in FIG. 7A.

One type of beam splitter is shown in FIG. 7A. Beam splitter 250 receives an incident light beam IL and color filter 255 filters out the shorter wavelength components of IL to form filtered beam CIL. The top curve in FIG. 7B shows the spectral transmittance curve for filter 255.

When beam CIL strikes the red reflective dichroic coating layer 260 of beam splitter 250, it divides into two component beams. The first beam, CIL 1, is reflected from coating 260 and has the spectral transmittance shown in the middle curve of FIG. 7B. The second beam, CIL 2, passes through dichroic coating layer 260 and has the spectral transmittance curve shown in the lowest curve of FIG. 7B.

Figure 7C:
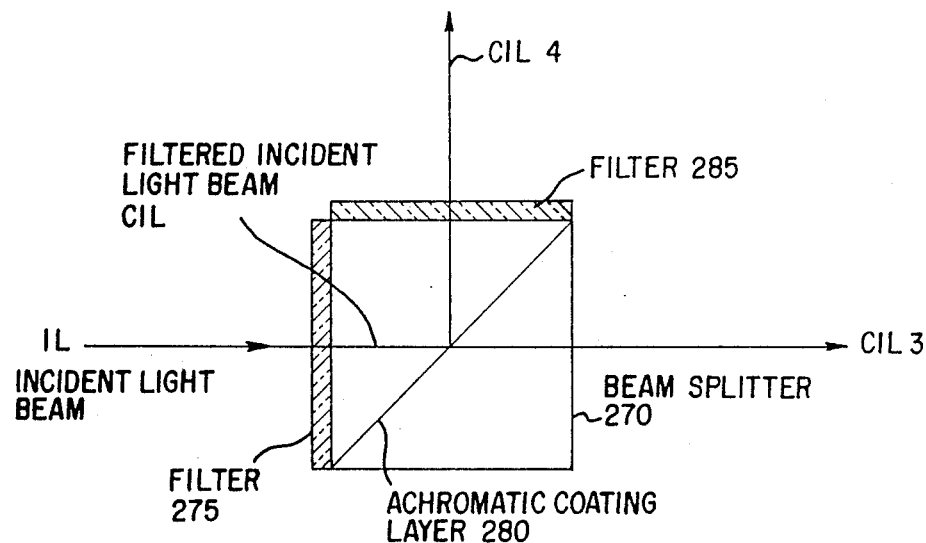
FIG. 7C shows another beam splitter.
Figure 7D:
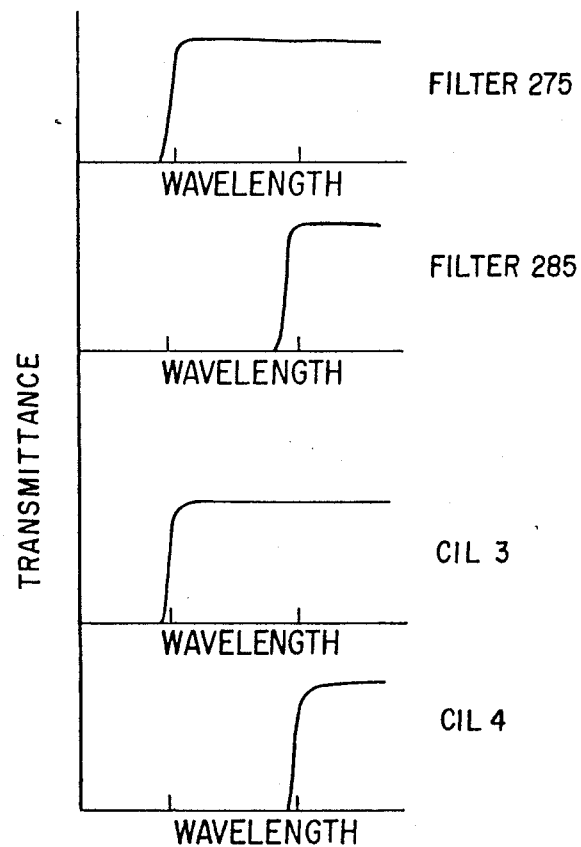
FIG. 7D shows spectral transmittance curves for the beam splitter in FIG. 7C.

FIG. 7C shows an alternative beam splitter which can be used instead of the beam splitter in FIG. 7. Incident light beam IL enters beam splitter 270 via color filter 275. The top curve of FIG. 7D shows the transmittance characteristic of color filter 275. The filtered incident light beam, CIL, then strikes achromatic coating layer 280 and is split into two beams, CIL 3 and CIL 4. CIL 3 passes through coating layer 280 and exits beam splitter 270 without passing through a filter. CIL 4 is reflected through color filter 285 whose transmittance curve is shown as the second curve in FIG. 7D. The spectral transmittance curves of CIL 3 and CIL 4 are shown as the third and fourth curves, respectively, of FIG. 7D.

Figure 9:
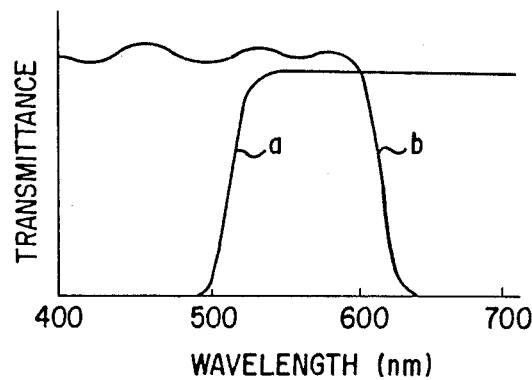
FIG. 9 shows the transmittance of the filter in FIG. 8.
Figure 8:
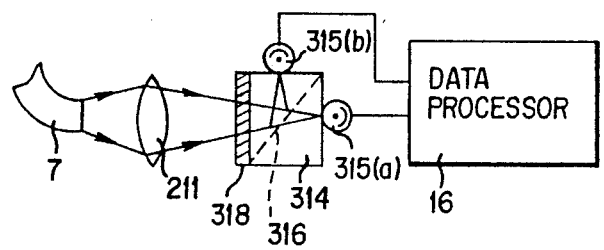
FIG. 8 is a diagram of a variation of the embodiment in shown in FIG. 7.

Instead of detecting all three components of the reflected light as in the embodiment shown in FIG. 7, the embodiment shown in FIG. 8 detects only the components of the reflected light in the medium and long wavelength zones. The operation of beam splitter 314 is similar to that shown in FIG. 7A. The reflected light passes through light condensor 211 and then through colored glass filter 318 which has the sharp cut-off characteristics of a short wavelength cut-off type filter. FIG. 9, curve a, shows the transmittance characteristics of filter 318. The filtered light then strikes either photodetector 315(a) or 315(b), according to reflecting surface 316 of prism type beam splitter 314. Similar to the apparatus of FIG. 7, the reflecting surface 316 is a red-reflecting dichroic mirror that reflects light with wavelengths greater than 630nm. Its spectroscopic transmittance is shown by curve b in FIG. 9.

Photodetector 315(a) detects the component of light that passes through reflecting surface 316 or, in other words, the component in the medium wave length zone. Photodetector 315(b) detects the component of light that is reflected by surface 316 or, in other words, the component in the long wavelength zone. Data processor 16 then computes the ratio $i_y/i_k$ or the difference $i_y$ minus $i_k$, since the $i_r$ component is unavailable.

The present invention is not limited to the embodiment described above. For example, the sharp-cut filters used to detect the proportions of reflected light in the different wavelength zones could be obtained by using color filters or interference filters possessing the necessary spectral transmissions or by spectrophotometrically dispersing the reflected light and then detecting the amount of light in the different wavelength zones. Also flat beam splitters could also be used instead of prism-type beam splitters.

Furthermore, the apparatus in FIG. 3 shows the detection of $i_O$ corresponding to the amount of reflected light passing uninterrupted into detector 115. This measurement is not indispensable, instead the ratio or difference between the reflected light and the different wavelength zones could be found directly from the components of the reflected light detected only through the two sharp cut-off filters.

Thus the present invention, in its broader aspects is not limited to the specific details, representative methods and apparatus, and illustrative examples shown and described. Departure may be made from such details without departing from the spirit or scope of the invention.

What is claimed is:

1. An apparatus for determining the thickness of a layer of copper oxide on an object comprising:
   illumination means producing a light having a known spectral distribution;
   illuminating light guide means for directing said light from said illumination means onto said object;
   reflecting light guide means for directing reflections of said light from said object to a first area;
   filter means mounted in said first area for filtering said reflected light received from said reflecting light guide means into two wavelength zones;
   determining means for receiving said reflected light filtered by said filter means and for measuring the quantities of said reflected light in said two wavelength zones; and
   calculating means for calculating a value representing a relationship of said reflected light quantities, and for thereby determining the thickness of said copper oxide layer on said object from a predetermined correspondence between copper oxide thicknesses and values for said relationship.

2. The apparatus of claim 1 wherein said illuminating means includes an incandescent light source and a reflective mirror mounted to direct light from said incandescent light source into said illuminating light guide means, and
   wherein both said illuminating and reflecting light guide means include optical fibers.

3. The apparatus of claim 2 further including a hot mirror mounted between said incadescent light source and said optical fiber in said illuminating light guide means.

4. The apparatus of claim 3 wherein said filter means includes
   a rotatable disk;
   two color filters mounted on said disk; and
   a motor coupled to said disk for rotating said color filters through said first area to intersect a path of said reflected light created by said reflecting light guide means.

5. The apparatus of claim 4 wherein said determining means includes a photodetector and wherein said calculating means includes a data processor coupled to said photodetector.

6. The apparatus of claim 5 further including means for transmitting information regarding the rate of rotation of said filters to said data processor.

7. The apparatus of claim 6 wherein said rate information transmitting means includes an LED and a second photodetector mounted on opposite sides of said rotating means, said rotatable disk also including at least one transparent portion located to allow light from said LED to strike said second photodetector at least once during each rotation of said filters.

8. The apparatus of claim 5 wherein said motor includes means, coupled to said data processor, for controlling the rate of rotation of said filters.

9. The apparatus of claim 4 wherein said two color filters are each sharp cut-off filters with transmission thresholds of approximately 500 nm and 630 nm, respectively.

10. The device of claim 1 wherein said filtering means includes:
    a first beam splitter having a first dichroic mirror splitting said reflected light into first and second beams; and
    a second beam splitter having a second dichroic mirror for splitting said second beam into third and fourth beams; wherein said determining means includes first through third photodetectors for receiving said first, third and fourth beams; and wherein said calculating means includes a data processor coupled to said first through third photodetectors.

11. The device of claim 1 wherein said filter means includes a color filter for filtering said reflected light and a beam splitter with a dichroic mirror for splitting said light reflections, after passing through color filter, into first and second beams; wherein said determining means includes first and second photodetectors mounted to receive said first and second beams; and wherein said calculating means includes a data processor coupled to said first and second photodetectors.

12. The device of claim 1 wherein said filter means includes a first color filter to filter said reflected light, a beam splitter with an archromatic coating layer for splitting said light reflections, after passing through said first color filter, into first and second beams, and a second color filter mounted in the light path of said first beam; wherein said determining means includes first and second photodetectors mounted to receive said first and second beams; and wherein said calculating means includes a data processor coupled to said first and second photodetectors.

13. A system for testing manufacturing items coated with copper oxide comprising:
    means for applying a copper oxide coating to said items;
    means for moving said items through said copper oxide coating means;
    means for illuminating said items with light;
    means for determining the quantities of reflected light by said items in different wavelength zones after said items have passed through said applying means; and
    means, coupled to said determining means, for calculating a value representing a relationship between said quantities of reflected light and for thereby determining the thickness of said copper oxide coating of said items from a predetermined regular relationship between copper oxide coating thicknesses and values for said relationship.

14. The system of claim 13 wherein said calculating means includes means for calculating a value for the ratio of said quantities of reflected light.

15. The system of claim 13 wherein said calculating means includes means for calculating a value for the difference between said quantities of reflected light.

16. The device of claim 13 wherein said determining means includes two beam splitters, each with a dichroic mirror, for splitting said reflected light into three beams, and three photodetectors mounted to receive said three beams.

17. The device of claim 13 wherein said determining means includes a color filter mounted to filter said reflected light, a beam splitter with a dichroic mirror for splitting said filtered reflected light into two beams, and two photodetectors mounted to receive said two beams.

18. The device of claim 13 wherein said determining means includes a first color filter mounted to filter said reflected light, a beam splitter with an achromatic reflecting surface for splitting said filtered reflected light into two beams, a second color filter mounted in the light path of one of said two beams and two photodetectors mounted to receive said two beams.

19. A method for determining the thickness of a copper oxide coating on an object comprising the steps of:
measuring the quantity of light reflected by said object in different wavelength zones;
calculating a value for a relationship between said quantities of reflected light; and
comparing said value of said relationship to a predetermined regular correspondence between thickness values and relationship values thereby to determine the thickness of said copper oxide coating.

20. The method of claim 19 wherein said calculating step includes the step of calculating a value for the ratio of said quantities of reflected light.

21. The method of claim 19 wherein said calculating step includes the step of calculating a value for the difference between said quantities of reflected light.

22. A method for manufacturing items coated with copper oxide comprising the steps of:
applying a copper oxide coating to said items;
measuring the quantities of light reflected from said items in predetermined wavelength zones;
calculating a value for the relationship between said quantities of reflected light; and
determining the thickness of said copper oxide coating by comparing said value with a predetermined regular correspondence between values for thicknesses and values of said relationship 23. An apparatus for determining the thickness of a layer of copper oxide coating on an object comprising:
light means for illuminating said object with light;
spectrum means for receiving the illuminating light reflected from said object and for separating the reflected light into at least three wavelength zones;
determining means for measuring the quantities of said reflected light in each of said separate zones; and
calculating means, coupled to said determining means, for calculating a value representing a relationship between said measured quantities of reflected light in said wavelength zones, and for thereby determining the thickness of the coating of said object from a predetermined regular correspondence between oxide coating thickness and values for said relationship.

24. The apparatus of claim 23 wherein said wavelength zones are separated by borders at approximately 500nm and 630nm.

* * * * *